United States Patent
Kortenbach et al.

(10) Patent No.: US 6,193,718 B1
(45) Date of Patent: Feb. 27, 2001

(54) ENDOSCOPIC ELECTROCAUTERY INSTRUMENT

(75) Inventors: Juergen Andrew Kortenbach, Miami Springs; Michael Sean McBrayer; Robert Sixto, both of Miami, all of FL (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/095,307

(22) Filed: Jun. 10, 1998

(51) Int. Cl.[7] .................................................. A61B 18/18
(52) U.S. Cl. ................................................. 606/50; 606/45
(58) Field of Search ..................... 606/41, 45, 48–52, 606/205–208

(56) References Cited

U.S. PATENT DOCUMENTS

| | | |
|---|---|---|
| 2,002,594 | 5/1935 | Wappler et al. . |
| 2,200,322 | 5/1940 | Arnesen . |
| 5,114,423 * | 5/1992 | Kasprzyk ................................ 606/27 |
| 5,258,006 | 11/1993 | Rydell et al. . |
| 5,330,471 | 7/1994 | Eggers . |
| 5,342,381 | 8/1994 | Tidemand . |
| 5,352,222 | 10/1994 | Rydell . |
| 5,356,408 | 10/1994 | Rydell . |
| 5,391,166 | 2/1995 | Eggers . |
| 5,395,369 | 3/1995 | McBrayer et al. . |
| 5,396,900 * | 3/1995 | Slater et al. ........................... 128/751 |
| 5,423,814 | 6/1995 | Zhu et al. . |
| 5,456,684 | 10/1995 | Schmidt et al. . |
| 5,462,546 | 10/1995 | Rydell . |
| 5,496,317 | 3/1996 | Goble et al. . |
| 5,514,134 | 5/1996 | Rydell et al. . |
| 5,540,685 | 7/1996 | Parins et al. . |
| 5,569,243 | 10/1996 | Kortenbach et al. . |
| 5,571,100 * | 11/1996 | Goble et al. ........................... 606/41 |
| 5,573,534 * | 11/1996 | Stone .................................... 606/48 |
| 5,637,111 | 6/1997 | Sutcu et al. . |
| 5,658,281 | 8/1997 | Heard . |
| 5,860,975 * | 1/1999 | Goble et al. ........................... 606/45 |
| 5,885,281 * | 3/1999 | Urueta ................................... 606/45 |
| 5,935,126 * | 8/1999 | Riza ...................................... 606/51 |

FOREIGN PATENT DOCUMENTS

| | | |
|---|---|---|
| 196 50 150 A1 | 6/1997 | (DE) . |
| 0 572 131 A1 | 12/1993 | (EP) . |
| 0 717 966 A1 | 6/1996 | (EP) . |
| WO 96/27338 * | 9/1996 | (WO) . |

* cited by examiner

Primary Examiner—Michael Peffley
(74) Attorney, Agent, or Firm—Finnegan, Henderson, Farabow, Garrett & Dunner, L. L. P.

(57) ABSTRACT

This invention relates to endoscopic electrocautery instruments for performing surgery on the tissue of a patient and passing current through the tissue to cause cauterization thereof. The instrument has a proximal end and a distal end and includes an elongated tube, a push rod located within the elongated tube, and a first and second end effector located adjacent a distal end of the elongated tube and controlled for relative movement by the push rod. Various arrangements are disclosed for creating a first and second cautery current path from the instrument proximal end to the first and second end effectors. In accordance with the invention, the end effectors are formed as scissor blade members having various conductive and non-conductive layer arrangements. The layer arrangements of the scissor blade members allow for different cauterization affects. Coupling arrangements between the blade members and the elongated tube are also disclosed.

39 Claims, 10 Drawing Sheets

ENDOSCOPIC ELECTROCAUTERY INSTRUMENT

BACKGROUND OF THE INVENTION

1. Field of the Invention

This invention relates to surgical apparatus, and more particularly to endoscopic electrocautery instruments such as bipolar scissors.

2. Description of Related Art

Endoscopic surgery is widely practiced throughout the world today and its acceptance is rapidly growing. Much of the popularity of endoscopic surgery can be attributed to its a less invasive, less traumatic affect upon the patient in comparison with standard open type surgery.

One type of endoscopic surgery involves placing trocar tubes into the patient through incisions and inserting endoscopic surgical tools through the trocar tubes for performing operations at a surgery site. A camera, magnifying lens, or other optical instrument is often inserted through one trocar tube, while a cutter, dissector, or other surgical instrument is inserted through the same or another trocar tube. The cutter, dissector, or other instrument is used to manipulate and/or cut tissue or organs of the patient. It may be desirable to utilize several trocar tubes at once to receive numerous surgical instruments. In this manner, a patient's organs or tissue may be, for example, grasped with one surgical instrument and simultaneously cut with another, all under the view of the surgeon via an optical instrument inserted through a trocar tube.

Various types of endoscopic surgical instruments are known in the art. Certain of these instruments may generally include an elongated, slender tube containing a push rod which is axially movable within the tube by way a handle or trigger-like actuator. An end effector is normally provided at the distal end of the tube and is coupled to the push rod so that axial movement of the push rod translates to rotational or pivotal movement of the end effector. End effectors may be, for example, scissor blades, grippers, cutting jaws, or forceps.

Modem endoscopic procedures often control a patient's bleeding in the surgical site through the use of electrocautery. Electrocautery passes cautery current to the surgery site to cauterize open blood vessels. Beyond reducing blood loss, electrocautery aids the operation by providing a clearer view of the surgical site. As used herein, the phrases cautery, electrocautery, and coagulation are interchangeable.

Several types of electrocautery instruments for use in endoscopic surgery have been described. One category of endoscopic electrocautery instruments is bipolar devices. Bipolar electrocautery instruments generally include two electrodes closely spaced for contact with organs and tissue of the patient. Typically, a bipolar electrocautery instrument includes two end effectors, one end effector acting as a first electrode, and the other end effector acting as a second electrode. The electrodes are electrically isolated from each other and include a separate current path back through to a current connector located adjacent the handle of the instrument. Thus, during contact of the bipolar instrument with an organ or tissue of the patient, current flows from the first end effector electrode, through the tissue to be cauterized, to the second end effector electrode of the bipolar instrument.

One type of bipolar electrocautery instrument used in endoscopic surgery is bipolar scissors. Bipolar scissors include first and second electrodes formed about scissor blade shaped end effectors. In operation, the end effectors cut tissue of the patient while cauterizing severed blood vessels at the surgery site.

Various problems have been encountered in the design, manufacture, and use of endoscopic electrocautery instruments. These problems include maximizing the current flow to the intended cauterizing area, maintaining a constant current supply to the end effectors, and manufacturing a reliable instrument for a reduced manufacturing cost and long life.

SUMMARY OF THE INVENTION

An object of this invention is to provide a reliable endoscopic electrocautery instrument of low manufacturing cost and improved cauterization that maintains the desired efficiency of the end effectors.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises an endoscopic electrocautery instrument for performing surgery on tissue of a patient and passing current through the tissue to cause cauterization thereof. The instrument has a proximal end and a distal end and includes a proximal actuator, an elongated tube having a proximal end connected to the actuator and a distal end, a push rod extending through the elongated tube and including a proximal end connected to the actuator, a first and second end effector located adjacent the elongated tube distal end and connected to the push rod to provide relative movement of the first and second end effectors upon actuation of the proximal actuator, a first current path passing cautery current from the instrument proximal end to an end effector first portion, and a second current path insulated from the first current path passing cautery current from the instrument proximal end to an end effector second portion, the first current path including the elongated tube and the second current path including the push rod.

In accordance with another aspect, the present invention comprises an endoscopic electrocautery instrument for performing surgery on tissue of a patient and passing current through the tissue to cause cauterization thereof. The instrument has a proximal end and a distal end and includes a proximal actuator, an elongated tube having a proximal end connected to the actuator and a distal end, a push rod having a proximal end connected to the actuator and located within the elongated tube, a first and second end effector located adjacent the elongated tube distal end and connected to the push rod to provide relative movement of the first and second end effectors upon actuation of the proximal actuator, a first electric connection including the elongated tube for supplying cautery current to an end effector first portion, and a second electric connection including the push rod for supplying cautery current to an end effector second portion.

In accordance with yet another aspect, the present invention includes an endoscopic electrocautery instrument for performing surgery on tissue of a patient and passing current through the tissue to cause cauterization thereof. The instrument has a proximal end and a distal end and includes a proximal actuator, an elongated tube having a proximal end connected to the actuator and a distal end, a first conductive rod connected to an uninsulated portion of the elongated tube, a second conductive rod connected to the actuator and located within the elongated tube, and a first and second end effector located adjacent the elongated tube distal end and connected to the second conductive, rod to provide relative movement of the first and second end effectors upon actuation of the proximal actuator.

In accordance with another aspect, the present invention includes an endoscopic electrocautery instrument for performing surgery on tissue of a patient and passing current through the tissue to cause cauterization thereof. The instrument has a proximal end and a distal end and includes a proximal actuator, an elongated tube having a proximal end connected to the actuator and a distal end, a push rod extending through the elongated tube and including a proximal end connected to the actuator, a first and second blade members located adjacent the elongated tube distal end and connected to the push rod to provide relative movement of the first and second blade members upon actuation of the proximal actuator. The scissor blade members each include an inner conductive layer having a cutting edge and an inner shearing surface, an outer conductive layer, and an intermediate non-conductive layer insulating the inner conductive layer from the outer conductive layer.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of the specification, illustrate several embodiments of the invention and together with the description, serve to explain the principals of the invention. In the drawings.

DETAILED DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

Figure 1:
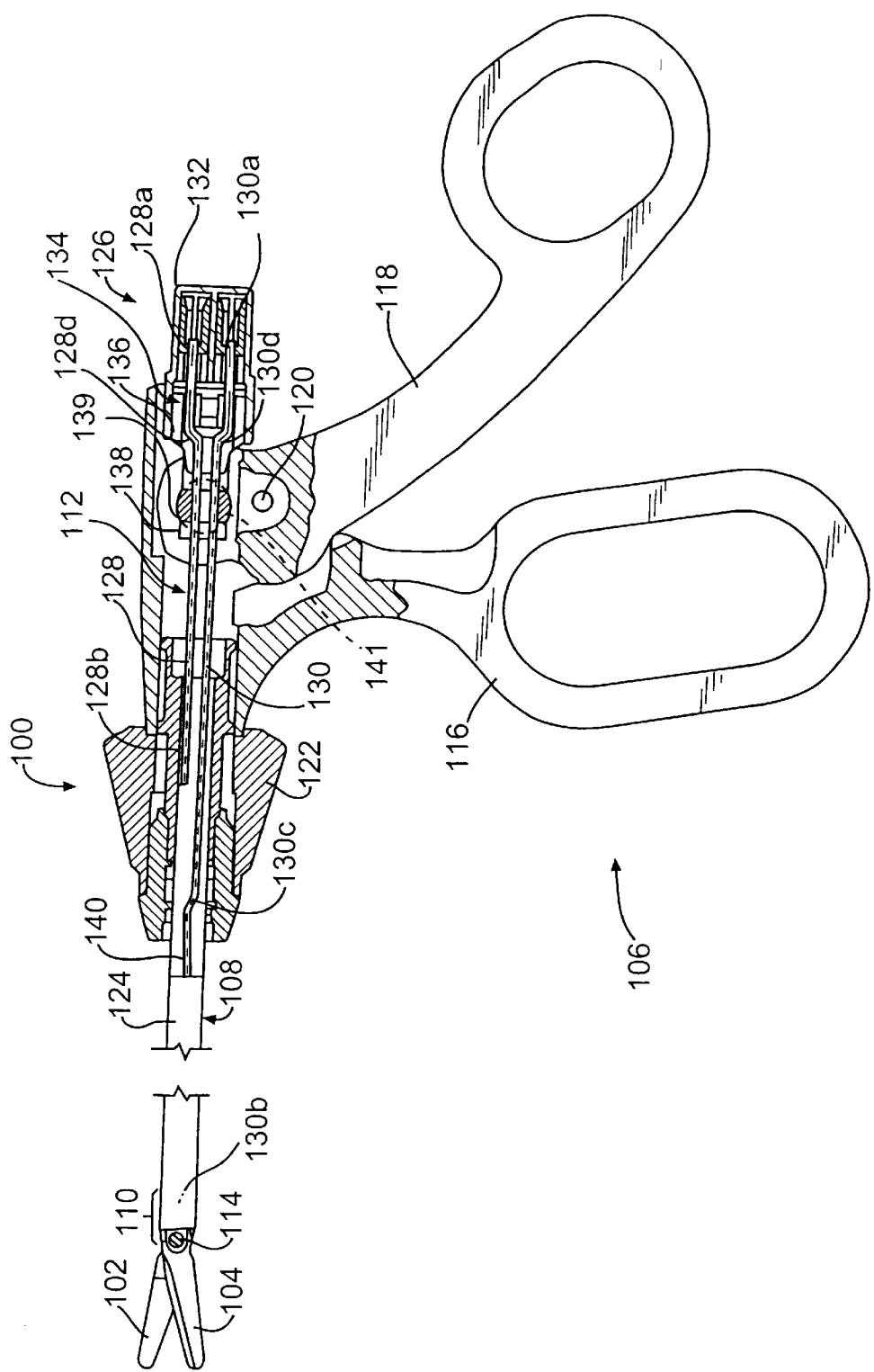
FIG. 1 is a broken partial section side view of an endoscopic electrocautery instrument according to a first embodiment of the present invention.

In accordance with the present invention, and as embodied herein, a first embodiment of an endoscopic electrocautery instrument, generally indicated at 100 in FIG. 1, includes a pair of end effector scissor blade members 102, 104 a proximal actuator 106, a hollow tube 108, a clevis area 110, and a rod assembly 112 extending through the tube. As described more fully below, at least one of the blade members 102, 104 is rotatably mounted in the clevis area 110 about a screw 114 and coupled to the distal end of the rod assembly 112. Those skilled in the art will appreciate that actuation of the actuator 106 causes the scissor blade members 102, 104 to move relative to one another to perform a cutting operation.

The proximal actuator 106 of the instrument 100 includes a fixed proximal handle 116 with a manual lever 118 pivotally coupled to the handle by a pivot pin 120. The elongated, hollow tube 108 is preferably made from stainless steel or other suitable material, and extends from the handle 118 to the clevis area 110. The tube 108 is preferably rotatably coupled about its longitudinal axis relative to the handle 116 through the use of a ferrule 122 such as described in detail in co-owned U.S. Pat. No. 5,569,243, the complete disclosure of which is herein incorporated by reference. The tube 108 is preferably covered with an insulating sheath 124 along substantially its entire length from the ferrule 122 to the clevis area 110. The rod assembly 112 extends into the hollow tube 108 and is coupled at its proximal end 126 to the manual lever actuator 118. The rod assembly 112 includes a pair of rods 128, 130 preferably made from stainless steel or any other suitably rigid material. Rod 130 of the rod assembly 112 acts as a push rod for the scissor blade members 102, 104 such that reciprocal movement of the rod assembly 112 relative to the tube 108 results in a scissor movement between the scissor blade members 102, 104, as shown for example in FIGS. 10 and 11. The reciprocal movement of the rod assembly 112 relative to the tube 108 is affected by movement of the manual lever actuator 118 relative to the handle 116.

The rods 128, 130 have proximal ends 128a, 130a and distal ends 128b, 130b. As described in co-owned U.S. patent application Ser. No. 08/530,741, the complete disclosure of which is herein incorporated by reference, the proximal ends 128a, 130a of the rods have divergent bends which cause the rods to terminate in parallel proximal pins of an electric cautery connector 132. The proximal ends of the rods, with the exception of the pins, are provided within a proximal collar 134. The proximal collar 134 has an increased diameter proximal portion 136 which accommodates the proximal bent portions 128d, 130d of the rods 128, 130 and a radial protrusion 138 which is located distally of the increased diameter portion 136. The radial protrusion 138 and the increased diameter portion 136 form a recess 139 therebetween for receiving a coupling portion 141 of the actuator 118. The proximal end of the collar 134 is provided with a snap-together coupling for receiving the female electric cautery connector 132. When assembled, the electric cautery connector 132 receives a standard male cautery plug (not shown).

The proximal collar 134 may be formed about the rods 128, 130 by an injection molding process, but is preferably produced by placing the proximal ends 128a, 130a of rods 128, 130 into open receiving grooves of a partially molded proximal collar and applying ultra violet curing material over the rods and grooves. The partially molded collar is then placed under ultra violet light so that the curing material quickly hardens to form the remaining portion of the proximal collar 134.

According to the first embodiment of the present invention, the distal end 128b of the stainless steel rod 128 terminates inside the hollow conductive tube 108 preferably at or near the proximal actuator 106. End 128b is swaged to make a wiping or sliding electrical contact with the conductive tube. Thus, as lever 118 is moved relative to handle 116, the distal end 128b of the rod 128 will move relative to the tube 108 and will make a wiping connection. It is to be understood that rod 128 may terminate at any point along tube 108 prior to clevis area 110.

As previously mentioned, the distal end 130b of the push rod 130 is connected to blade members 102, 104 so that axial movement of the push rod causes a scissor movement of the blade members 102, 104. Preferably, the push rod 130 is provided with an insulating sheath 140 from the clevis area 110 at the distal end 130b to the proximal collar 134. Sheath 140 ensures that push rod 130 is electrically isolated from rod 128 and tube 108. As shown in FIG. 1, the push rod 130 is swaged at a point 130c distal of the distal end 128b of the rod 128 so that it assumes a substantially co-axial relationship with the tube 108.

In operation, the endoscopic electrocautery instrument of FIG. 1 provides two cautery current paths to the scissor blade members 102, 104. The first path travels from the electric cautery connector 132 along the stainless steel rod 128 to the tube 108 and then across the clevis area 110 to at least one scissor blade member 102, 104. The second current path flows from the electric cautery connector 132 to the push rod 130 and then to at least one scissor blade member via a coupling arrangement between the push rod 130 and scissor blade members 102, 104. The blade member coupling arrangement that permits the two cautery current paths will be described in detail with reference to FIGS. 10 through 16 below. In addition, FIGS. 4 through 9 also to be described below, detail the various embodiments of blade members for use in connection with the two cautery current paths to produce the desired cauterization at the surgery site.

Figure 2:
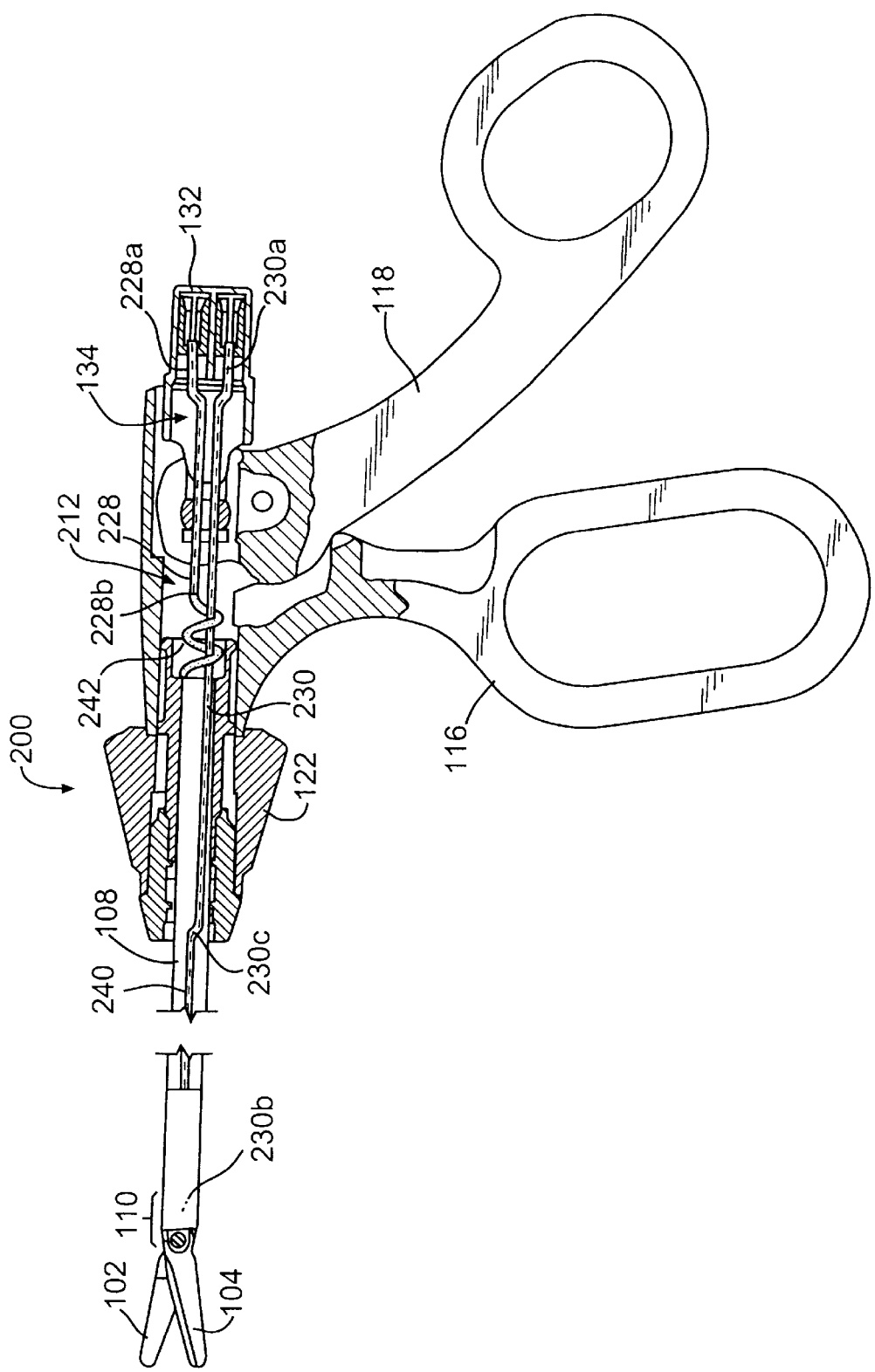
FIG. 2 is a broken partial section side view of an endoscopic electrocautery instrument according to a second embodiment of the present invention.

FIG. 2 shows a second embodiment of an endoscopic electrocautery instrument according to the present invention. Instrument 200 is similar to instrument 100 of FIG. 1 described above but with a different rod assembly 212. The rod assembly 212, according to this embodiment, includes a pair of rods 228, 230 once again preferably made from stainless steel. Rods 228, 230 have proximal ends 228a, 230a and distal ends 228b, 230b. The proximal ends 228a, 230a of the rods have divergent bends which cause the rods to terminate in parallel proximal pins. The proximal ends of the rods, with the exception of the pins, are provided with an over-molded proximal collar 134 which is substantially the same as described above with reference to FIG. 1.

According to the second embodiment of the invention, the distal end 228b of the first stainless steel rod 228 terminates at a point proximal of the hollow conductive tube 108 and is connected to the hollow conductive tube 108 (preferably at the proximal end of the tube) by an extendable coiled wire or spring 242. The connections between the wire 242 and the tube 108, and the wire 242 and rod 228 may be accomplished by soldering clips, or other secure fastening or connection arrangements known in the art.

Similar to the embodiment of FIG. 1, the push rod 230 is preferably provided with an insulating sheath 240 from the clevis area 110 at the distal end thereof to the proximal collar 134, and the push rod 230 is swaged at a point 230c distal of the distal end 228b of the rod 228 so that the push rod 230 assumes a substantially co-axial relationship with the tube 108. The push rod 230 is coupled to the scissor members 102, 104 in a manner similar to that of the embodiment of FIG. 1 and to be described in detail below.

In operation, the endoscopic electrocautery instrument of FIG. 2 provides two cautery current paths to the scissor blade members 102, 104. The first current path travels from the electric cautery connector 132 along the stainless steel rod 228 to the extendable coiled wire or spring 242 to the tube 108 and then across the clevis area 110 to at least one of the scissor blade members. When the lever 118 is moved relative to the handle 116, the rod assembly 212 will move relative to the tube 108 and the coiled wire or spring 242 will provide the necessary slack between the fixed proximal end of the tube 108 and the moving distal end 228b of the rod 228. The second cautery current path is substantially the same as that described in relation to the embodiment of FIG. 1.

As described regarding the endoscopic electrocautery instrument of FIG. 1, the tube 108, scissor blade members 102, 104 and push rod assembly 212 are freely rotatable relative to the handle 116 and lever 118 via use of the ferrule assembly 122, as described in previously incorporated co-owned U.S. Pat. No. 5,569,243.

Figure 3:
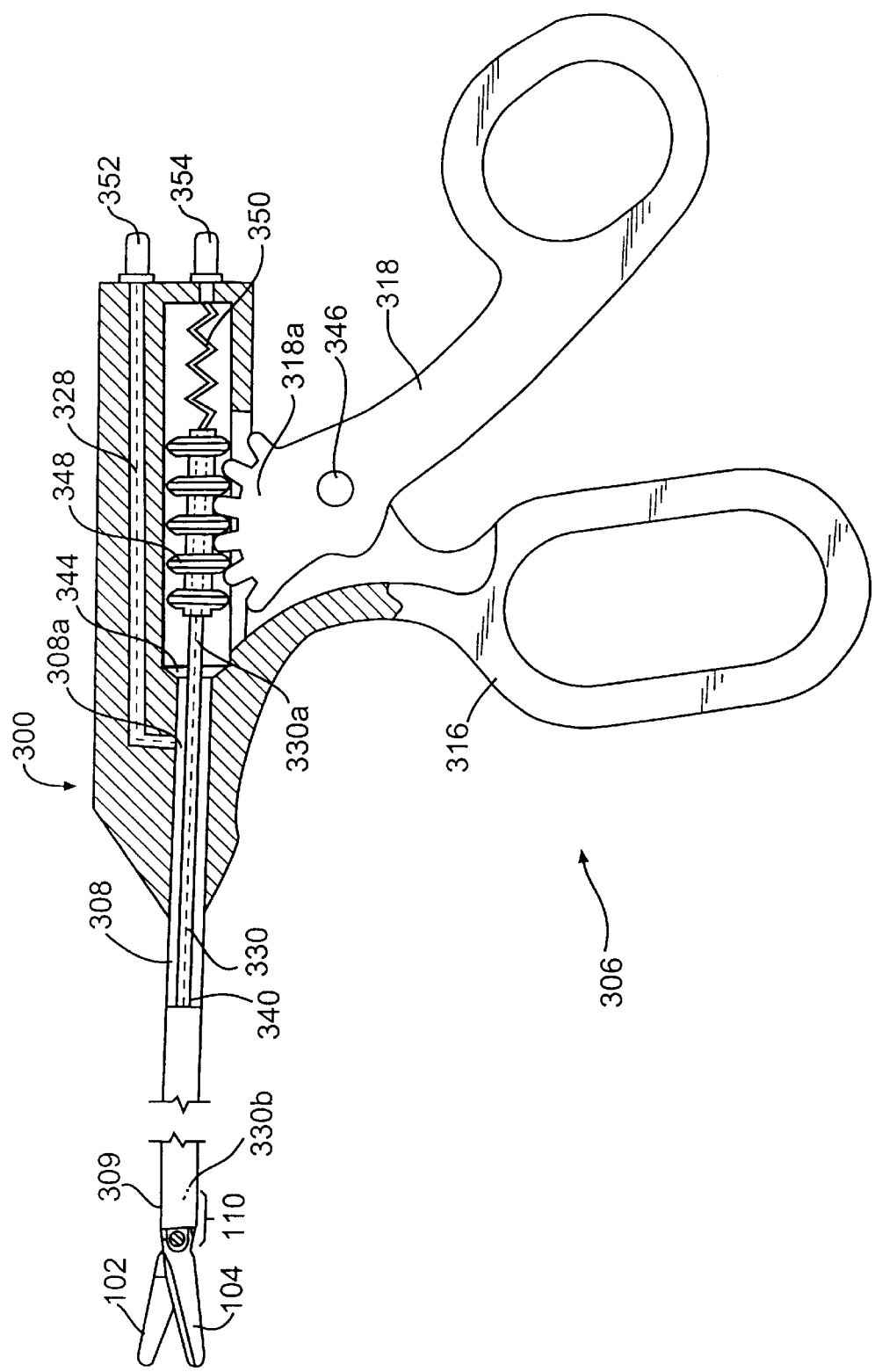
FIG. 3 is a broken partial section side view of an endoscopic electrocautery instrument according to a third embodiment of the present invention.

According to a third embodiment of the present invention, the endoscopic electrocautery instrument 300 of FIG. 3 includes a manual actuator 306 having a non-conductive handle 316 including a stepped throughbore 344 and a lever 318 rotatably coupled to the handle 316 by a pivot pin 346. The lever 318 has an upper pinion gear 318a which extends into the throughbore 344. The elongated tube 308 is fixedly coupled to a distal portion of the handle 316 about the throughbore 344 and extends to the clevis area 110. Between the throughbore 344 and a distal end of the handle 316, the tube 308 is contacted by a first electrical conductor 328 about the outer surface of the tube 308. The exterior surface of the tube 308 is preferably covered with an insulating sheath 309 along its length between the handle 316 and the clevis area 110.

The proximal end 330a of the push rod 330 is fixedly coupled by any suitable connection means to a slidable rack member 348 which is disposed in the throughbore 344 and is engaged by the pinion gear 318a of the lever 318. An expandable, electric conductor 350 (e.g. a spring or coil made of electrically conductive material) is electrically coupled to the proximal end 330a of the push rod 330 about the rack member 348. The proximal end of the handle 316 is provided with first and second electrical connectors 352, 354 which are respectively coupled to the first and second conductors 328, 350. The distal end 330b of the push rod 330 extends into the clevis area 110 and is coupled to the scissor blade members 102, 104 as described in detail below.

As in previous embodiments, the outer surface of the push rod 330 is preferably covered with an insulating sheath 340 along substantially its entire length from the rack member 348 to its distal end 330b. Rotation of the lever 318 relative to the handle 316 causes reciprocal movement of the push rod 330 relative to the tube 308 to affect a scissor movement between scissor blade members 102, 104.

In operation, the endoscopic electrocautery instrument of FIG. 3 provides two cautery current paths to the scissor blade members 102, 104. The first path travels from the electric cautery connector 352 along the electric conductor 328 to the outer surface of the tube 308 and then across the clevis area 110 to at least one scissor blade member 102, 104. The second current path flows from the electric cautery connector 354 to the expandable coil 350, to the proximal end of the push rod 330a located within the slide rack member 348, and then to at least one scissor blade member via a coupling arrangement between the push rod 330 and the scissor blade members 102, 104.

For purposes of manufacturing and assembly, it will be appreciated by those skilled in the art that the non-conductive handle 316 may be manufactured as two separate halves. Once the conductor 330, the tube 308, and the rack 348 are placed into one half of the handle, the two halves may be snapped, welded or otherwise coupled together.

FIGS. 4 through 9 detail various embodiments of scissor blade member configurations, the details of which are explained below. Each scissor blade configuration can be utilized in the endoscopic electrocautery instruments of FIGS. 1 through 3.

Figure 4:
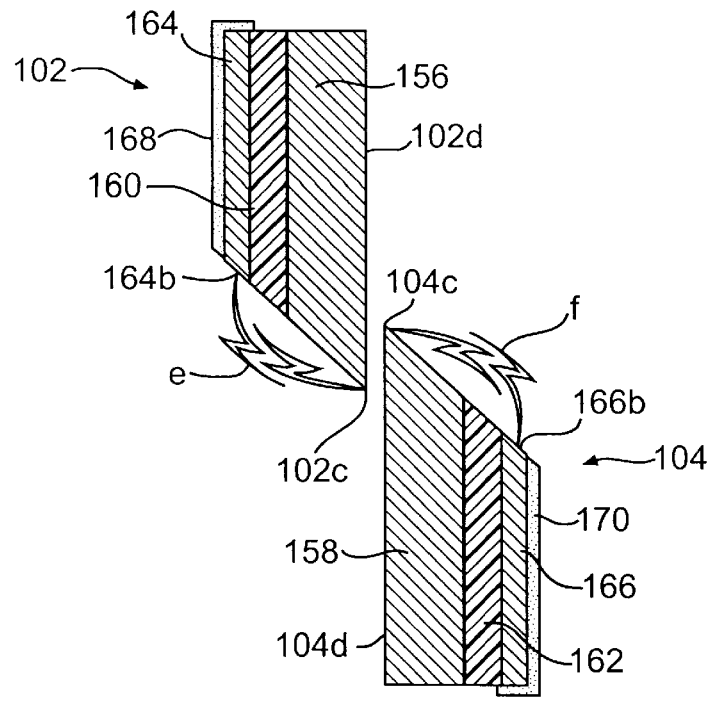
FIG. 4 is a cross-sectional view of a first pair of scissor blade members for use in the embodiments of FIGS. 1 through 3.

As shown in FIG. 4, a first set of scissor blade members 102, 104 is preferably composed of four layers: an inner conductive layer 156, 158, preferably formed of a superalloy or stainless steel, an intermediate non-conductive layer 160, 162, preferably epoxy or ceramic, an outer conductive layer 164, 166, preferably aluminum, and a non-conductive anodized aluminum layer 168, 170 on the outer surface of the outer conductive layer. As will be appreciated by those skilled in the art, any of the first three mentioned layers may be considered a primary substrate layer, although it is preferred that the substrate layer form the cutting edge of the blade. Thus, if either conductive layer were to be used as the primary substrate layer, a standard stainless steel or superalloy endoscopic scissor blade could be utilized for that layer. If the intermediate non-conductive layer is to be used as the primary substrate layer, it is preferably formed from ceramic. Other conductive and non-conductive layer arrangements are shown in co-owned U.S. patent application Ser. No. 08/354,992, the complete disclosure of which is herein incorporated by reference.

Regardless of the materials used, the inner conductive layer 156, 158 forms an inner face of the scissor blade members 102, 104, a shearing surface 102d, 104d, and a cutting edge 102c, 104c. The outer conductive layer 164, 166 forms an outer layer of the scissor blade members 102, 104 and is insulated from the first conductive layer by the intermediate non-conductive layer 160, 162. According to the invention, the outer conductive layer 164, 166 of each blade member is preferably made of aluminum which is "hard coated" or anodized to form the outer non-conductive layer 168, 170. Non-conductive layer 168, 170 has a relatively smaller thickness as compared to the outer layers and is shown in an exaggerated fashion in FIG. 4. The outer non-conductive layer 168, 170 covers substantially all of the outer conductive layer 164, 166 except for an end strip 164b, 166b which is closest to the cutting edge 102c, 104c and (as described in more detail below in relation to FIGS. 10–16) a portion in the vicinity of a scissor blade mounting hole. According to a presently preferred embodiment, the exposed strip 164b, 166b is formed by grinding subsequent to anodizing. Those skilled in the art will appreciate that anodizing is a process which causes an oxidized layer to form on the surface of aluminum. The process is performed by placing aluminum in an aqueous bath containing salts which react with the aluminum to form $Al_2O_3$. The outer non-conductive layer formed by anodizing is typically about 0.001 to 0.004 inches thick.

Referring back to the instrument shown in FIG. 1, application of a cautery current to the electrical connector 132 results in a first current being conducted from the push rod 130 to the inner conductive layers 156, 158 of the blade members 102, 104 and a second current of opposite polarity to the first current being conducted from push rod 128 to the tube 108 and to the outside layers 164, 166 of the blade members. The structure used to apply such currents will be described later with respect to FIGS. 10 to 16. When tissue is located between the cutting edge 102c and the exposed end strip 164b of the surface of the outer layer 164 of the blade member 102 as shown by the lines "e" (i.e., tissue which is in the process of being cut), current will flow through from one layer to the other through the tissue. Similarly, current will flow through tissue which is located between the cutting edge 104c and the exposed end strip 166b of the outer surface 166 of the blade 104 as shown by the lines "f". The hard coating layers 168, 170 on the outer conductive layers of the blade members prevents an inadvertent cauterization of other tissues near the surgical site. It will also be appreciated that the relatively small exposed end strips 164b, 166b result in a higher current density near the cutting edges of each blade member, which causes blood and saline solution that comes in contact with the blade member to be quickly and advantageously burned off.

Figure 5:
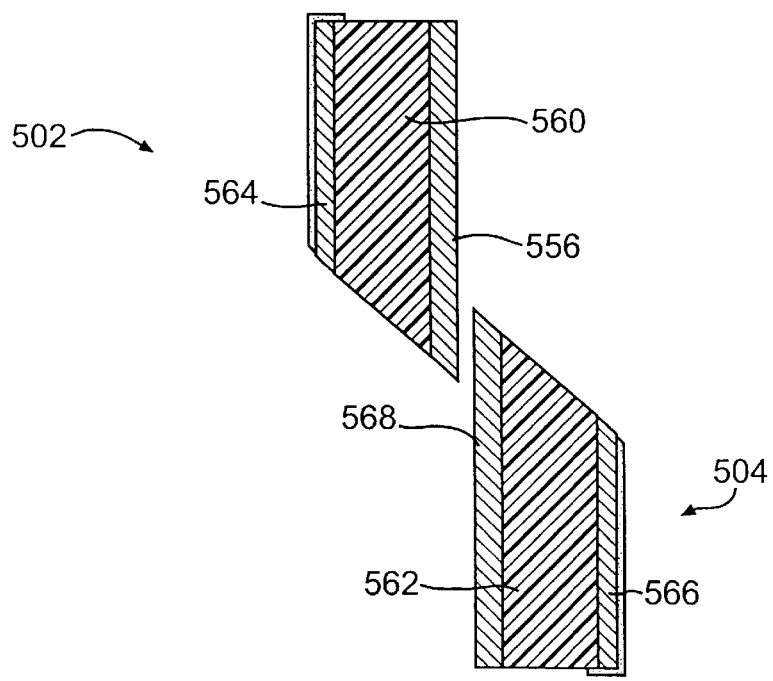
FIG. 5 is a cross-sectional view of a second pair of scissor blade members for use in the embodiments of FIGS. 1 through 3.

As seen FIG. 5, a second set of blade members 502, 504 is substantially the same as the blade members 102, 104 and will be described with reference numerals of similar elements increased by 400. The blade members 502, 504 differ from the blade members 102, 104 in that the substrate of each blade member is the intermediate non-conductive layer 560, 562 which is preferably ceramic. Both the inner conductive layer 556, 558 and the outer conductive layer 564, 566 of the blade members are preferably formed of deposited aluminum.

The scissor blade members described thus far each comprise four layers (including the layers formed by anodizing) and are substantially hermaphroditic, i.e. both blade members of a scissor instrument are substantially identical. Moreover, aspects of the present invention also relate to scissor blade members having fewer than four layers and to scissor instruments which have two non-identical blade members. Further, the present invention also applies to curved scissor blade members.

Figure 6:
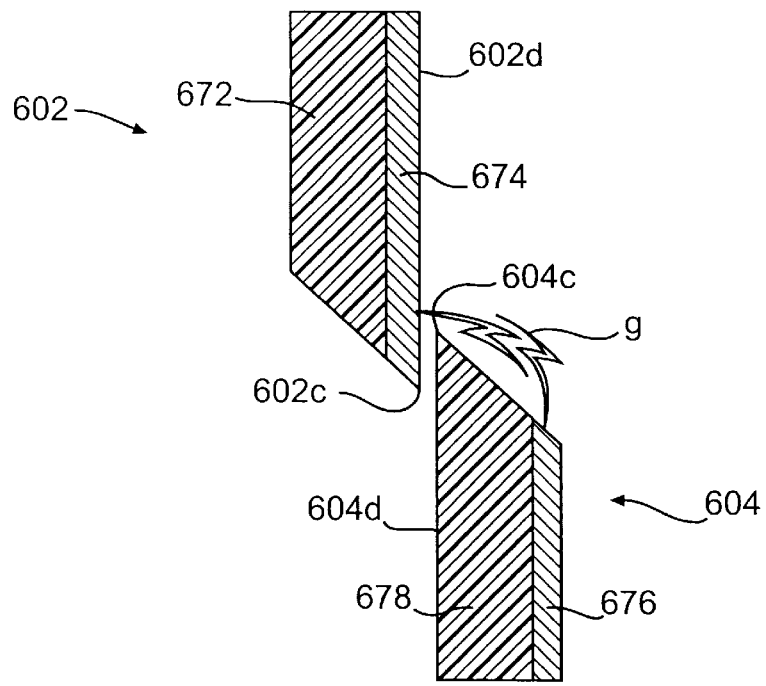
FIG. 6 is a cross-sectional view of a third pair of scissor blade members for use in the embodiments of FIGS. 1 through 3.

Turning now to FIG. 6, a third set of scissor blade members are formed with non-identical blade members 602, 604 each having one conductive layer and one non-conductive layer. The blade member 602 has a non-conductive outer layer 672 and a conductive inner layer 674 defining a cutting edge 602c and a shearing surface 602d. The blade member 604 has a conductive outer layer 676 and a non-conductive inner layer 678 defining a cutting edge 604c and a shearing surface 604d. As discussed below with reference to FIGS. 10–16, the inner conductive layer 674 of the blade member 602 makes electrical contact with a push rod having a first polarity and the outer conductive layer 676 of the blade member 604 makes electrical contact with an elongated tube on an endoscopic electrocautery instrument. Cautery current flows through tissue located between the cutting edge 602c and the shearing surface 602d of the blade 602 and the upper portion of the outer layer 676 of the blade 604 as shown by the lines "g". The scissor blade member arrangement shown in FIG. 6 may be particularly useful in "single acting" endoscopic scissors (as further described in accordance with the description of FIG. 16 below).

Although the scissor blade members are shown in FIG. 6 as having a relatively thick non-conductive layer and a relatively thin conductive layer, the relative dimensions of the layers can vary depending on the materials used to fabricate the blade members. Any of the fabrication methods and materials described above can be used to manufacture the scissor blade members shown in FIG. 6.

Figure 7:
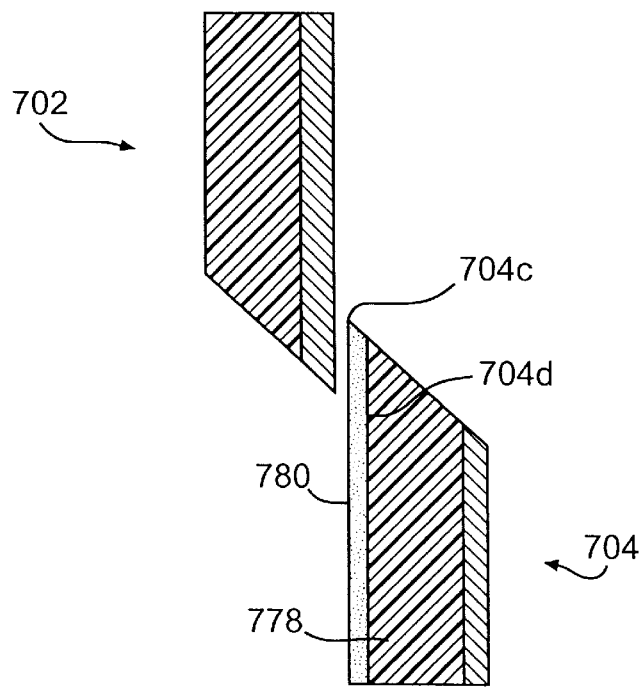
FIG. 7 is a cross-sectional view of a forth pair of scissor blade members for use in the embodiments of FIGS. 1 through 3.

Further, as shown in FIG. 7, a fourth set of scissor blade members are formed with non-identical blade members 702, 704. The blade members 702, 704 are similar to the blade members 602, 604 with the exception that an additional layer of alumina and titanium dioxide ($Al_2O_3/TiO_2$) or metal spray 780 is formed on the shearing surface 704d of the non-conducting inner layer 778. The alumina and titanium dioxide layer preferably has a weight ratio of 60%/40% alumina to titanium dioxide. The additional layer can be applied in any known manner as disclosed in co-owned U.S. patent application Ser. No. 08/429,596, the complete disclosure of which is herein incorporated by reference. The additional layer 780 (shown in an exaggerated fashion in FIG. 7) allows for improved machining of the cutting angle as compared to that of machining other non-conductive materials. Such improved machining allows for a sharper cutting edge 704c and therefore a more effective cutting action of the scissor blade members. It will be appreciated by those skilled in the art that the additional layer of alumina and titanium dioxide or metal spray will provide the above benefits on any scissor blade member having a ceramic shearing surface.

Figure 8:
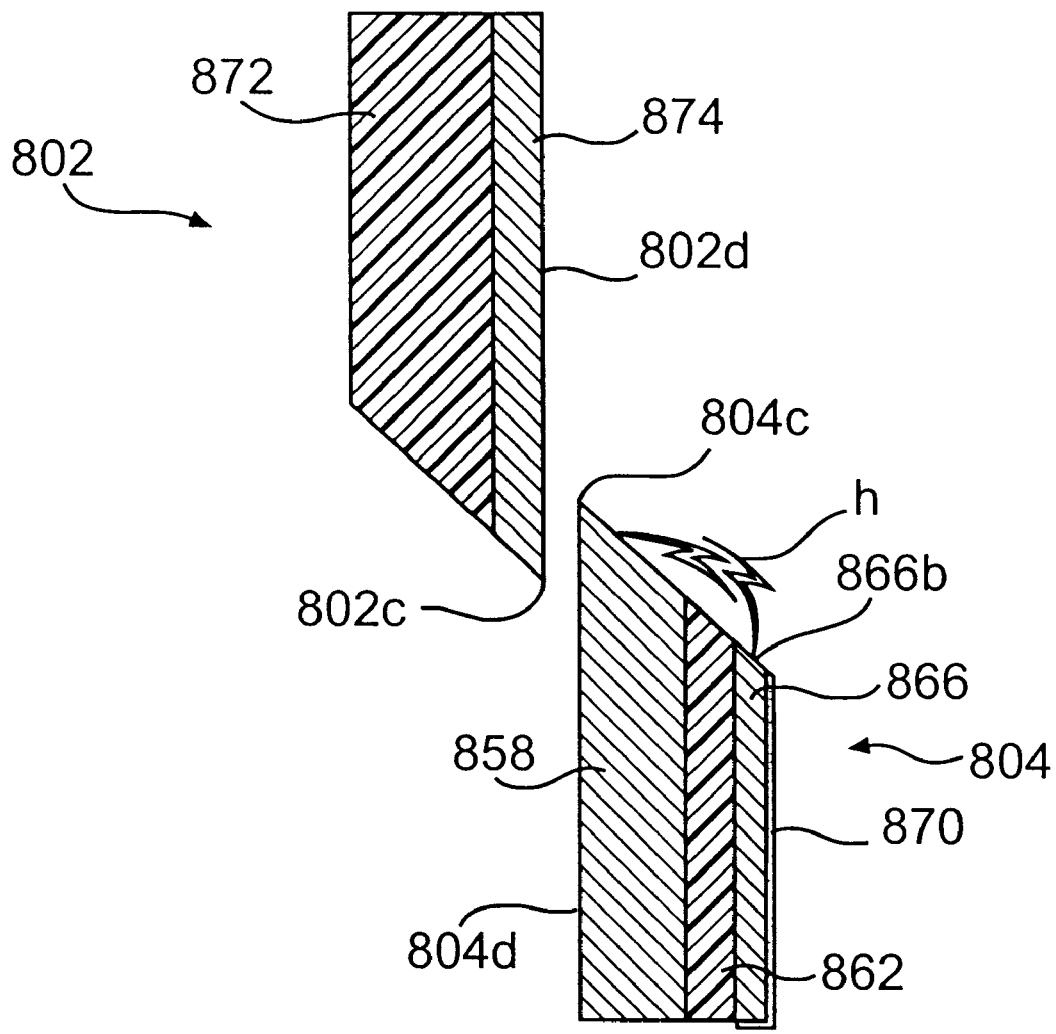
FIG. 8 is a cross-sectional view of a fifth pair of scissor blade members for use in the embodiments of FIGS. 1 through 3.

FIG. 8 shows a fifth set of scissor blade members according to the present invention. In this design, the scissor blade member 802 is substantially the same as scissor blade member 602 of the embodiment shown in FIG. 6, but m and scissor blade member 804 is similar to the scissor blade member 104 of the embodiment shown in FIG. 4. The blade member 802 has an outer non-conductive layer 872 and an inner conductive layer 874 that defines a cutting edge 802c and a shearing surface 802d. The blade member 804 has an inner conductive layer 858 that defines a cutting edge 804c and a shearing surface 804d, an intermediate non-conductive layer 862, and an outer conductive layer 866. The outer conductive layer 866 is anodized to form a non-conductive layer 870 which is ground along a portion 866b to form an end strip adjacent to the cutting edge 804c. The path of cautery current flows along the path of least resistance from the cutting edge 804c to the ground portion 866b as shown by lines "h". One significant difference between the blade members of FIG. 8 and the blade members of FIG. 6 is that the blade members of FIG. 8 provide two metallic cutting edges and shearing surfaces. It is generally considered advantageous that the cutting edges and shearing surfaces of both blade members be metallic to provide for both a feel of conventional scissors during the cutting operation and the most effective cutting angle. Blade member 802, being electrically connected to conductive layer 858, assists cauterization by also allowing cautery current flow between outer conductive layer 866 and conductive layer 874. Further, blade 802 can be formed of a single conductive material as long as cutting edge 802c is only electrically connected to inner conductive layer 858.

Figure 9A:
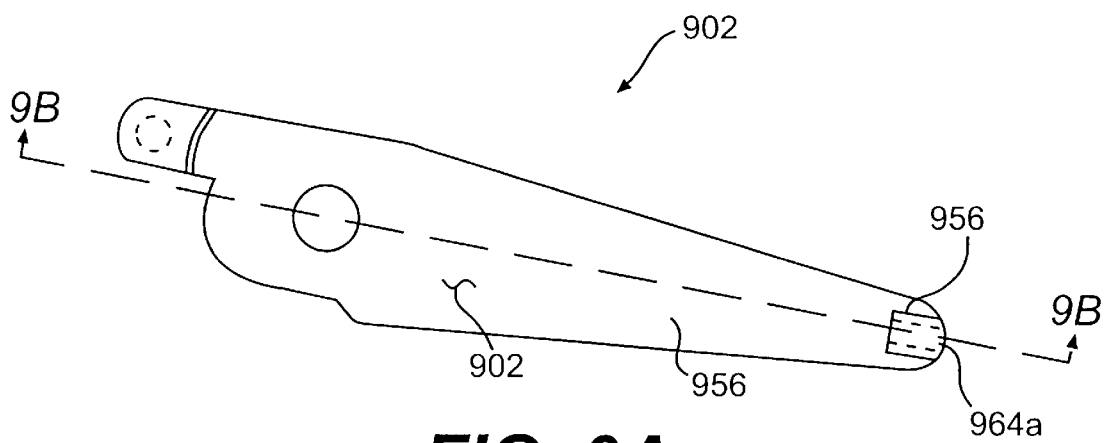
FIGS. 9A and 9B are views of a sixth scissor blade member for use in the embodiments of FIGS. 1 through 3.
Figure 9B:
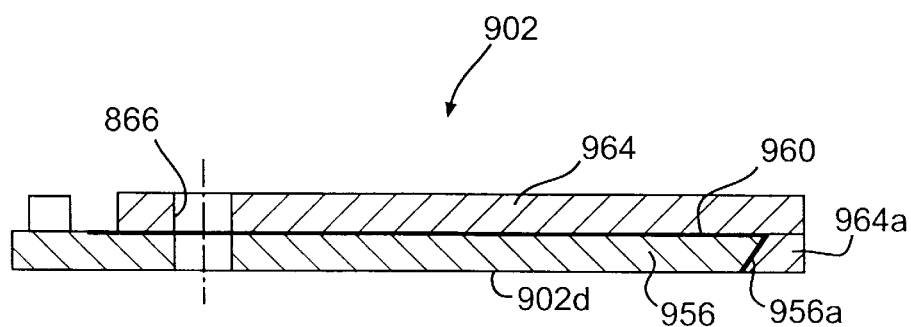

FIGS. 9A and 9B illustrate a sixth scissor blade member design in accordance with the present invention. As best seen in FIG. 9B, the scissor blade member 902 includes an inner conductive aluminum layer 956, an intermediate non-conductive layer 960, and an outer conductive metallic layer 964. The intermediate layer 960 is preferably formed by anodizing or hard coating the surface of the aluminum layer 956 opposite a shearing surface 902d. As described with reference to the above blade members 102, 104 the desired cauterization is affected by supplying a first current to the inner conductive layer 956 and a second current of opposite polarity to the outer conductive layer 964.

The two conductive layers 956, 964 of the scissor blade member 902 are interlocked together by a dovetail 964a protruding from the outer conductive layer 964 into a corresponding groove 956a of the inner conductive layer 956. The dovetail 964a tapers outwardly from the inner surface of conductive layer 964 to the shearing surface 902d of inner conductive layer 956. Such a mechanical coupling obviates any problems resulting from the use of epoxies. Scissor blade member 902 is secured at a proximal end adjacent a through hole 966 by a screw and clevis arrangement (described below).

The scissor blade members of FIGS. 4 through 9 are each capable of being coupled to any of the endoscopic electrocautery instruments of FIGS. 1 through 3. Using, for example, the endoscopic electrocautery instrument of FIG. 1 and the scissor blade members of FIG. 4, FIGS. 10 through 12 depict a first embodiment of a coupling arrangement of the blade members 102, 104 to the endoscopic electrocautery instrument 100.

Figure 10:
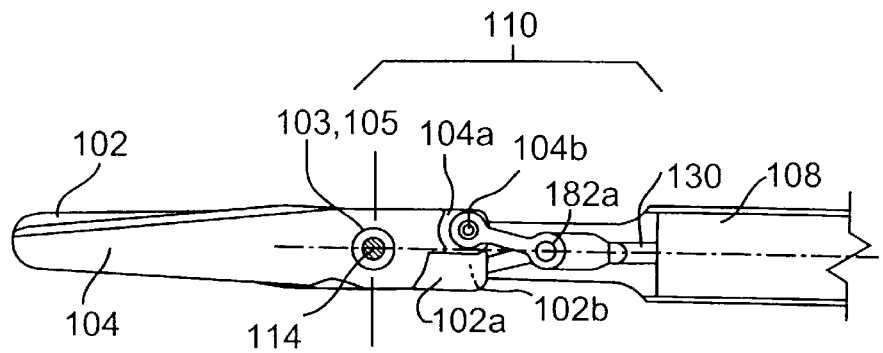
FIGS. 10 and 11 are partial section views of a first blade member coupling arrangement for use in the embodiments of FIGS. 1 through 3.
Figure 11:
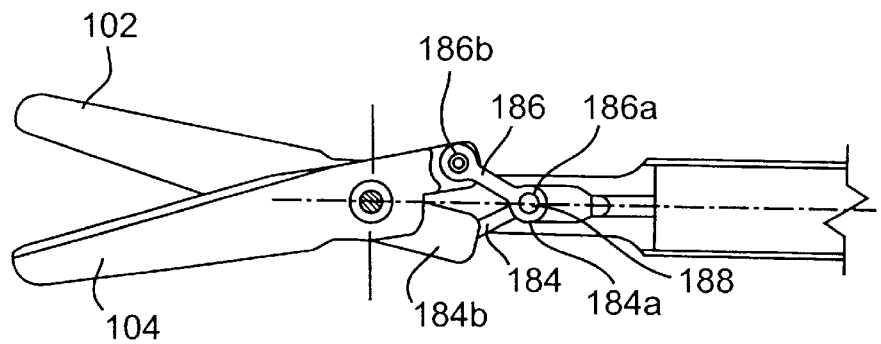
Figure 12:
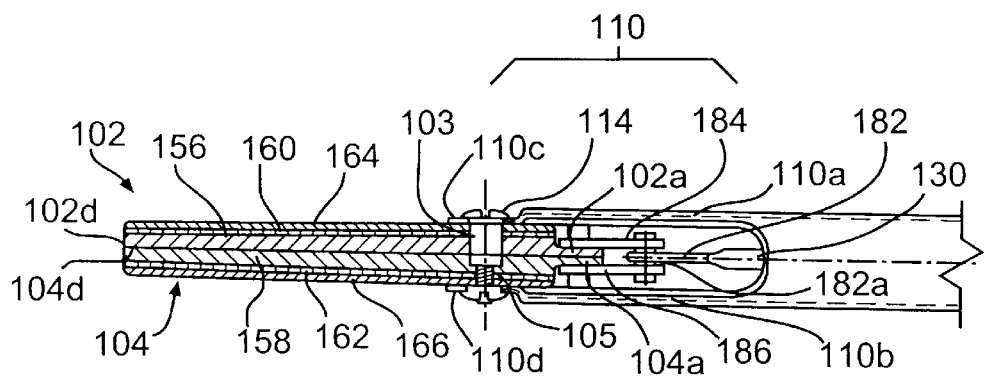
FIG. 12 is a partial section top view of the first coupling arrangement of FIGS. 10 and 11.

With reference to FIG. 10, the proximal end of each blade member 102, 104 includes a mounting hole 103, 105 a tang 102a, 104a and an orthogonal boss 102b, 104b. These elements connect the blade members 102, 104 with the clevis area 110 and the distal end of the push rod 130 to pivotally rotate the blade members relative to one another in response to movement of the lever 118. As shown in FIG. 12, the clevis area 110 includes a pair of distally extending arms 110a, 110b. Each arm 110a, 110b has an axle hole 110c, 110d for receiving a non-conductive screw 114. The push rod 130 extends through the tube 108 and into the space between the clevis arms 110a, 110b and includes a flattened end 182 defining a coupling hole 182a. Prior to mounting the scissor blade members 102, 104 in the clevis arms 110a and 110b, the tangs 102a, 104a of the blade members are coupled to the flattened distal end 182 of the push rod 130 using conductive links 184, 186. As shown in FIG. 11, the links 184, 186 have first and second holes 184a, 184b and 186a, 186b. The first holes 184a, 186a are coupled to the hole 182a in the flattened end 182 of the push rod 130 by a rivet 188. The second holes 184b, 186b are placed over bosses 102b, 104b which extend orthogonally from the tangs 102a, 104a of the scissor blade members 102, 104. Each boss 102b, 104b is located on the same layer of the scissor blade (i.e. the inner conductive layer 156, 158) and is electrically coupled with the shearing surface. It will therefore be appreciated that inner conductive layer 156, 158 of each blade member is electrically coupled to the conductive push rod 130.

Again with reference to FIG. 12, the scissor blade members 102, 104 are mounted in the clevis arms 110a, 110b with their shearing surfaces 102d, 104d facing each other and with their mounting holes 103, 105 aligned with the axle holes 110c, 110d of the clevis arms 110a, 110b. With the blade members so aligned between the arms 110a, 110b of the clevis, a non-conductive screw 114 is inserted through the holes 110c, 103, 105, and 110d. As mentioned above, a portion of the outer conductive layer 164, 166, of each scissor blade in the vicinity of the mounting hole 103, 105 is left uncoated (or is ground to remove the hard coating) so that the outer conductive layer makes electrical contact with the conductive clevis arms 110a, 110b and is electrically coupled to the conductive tube 108.

Figure 13:
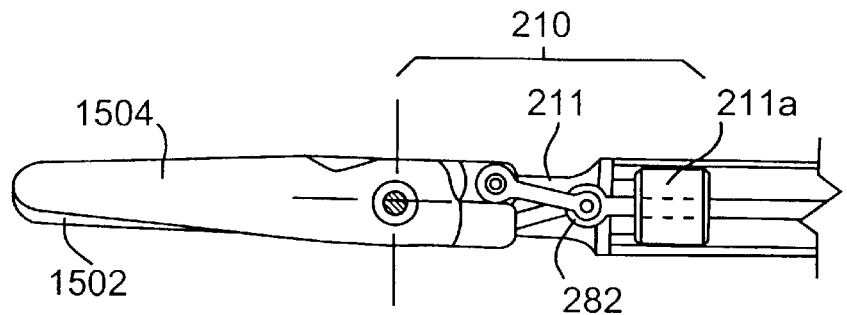
FIGS. 13 and 14 are partial section views of a second blade member coupling arrangement for use in the embodiments of FIGS. 1 through 3.
Figure 14:
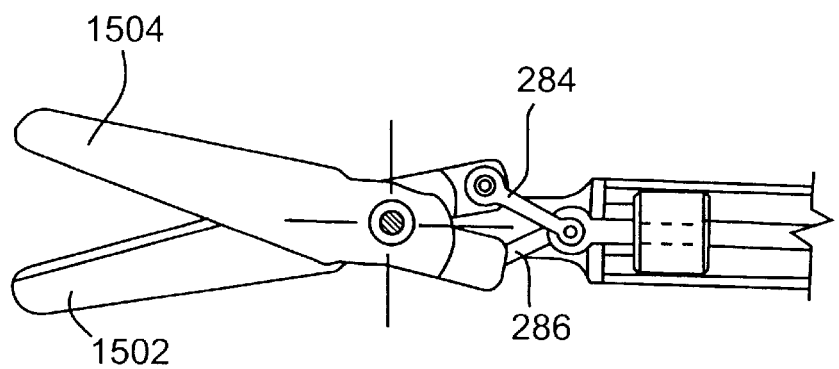
Figure 15:
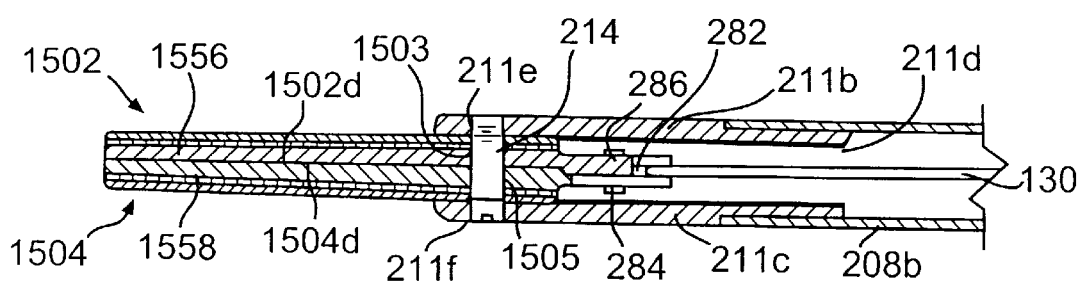
FIG. 15 is a partial section top view of the second coupling arrangement of FIGS. 13 and 14.

FIGS. 13 through 15 show a second embodiment of a coupling arrangement of the scissor blade members with the endoscopic electrocautery instrument of FIGS. 1 through 3. A conductive clevis area 210 includes a clevis member 211 having a proximal cylindrical base 211a, a pair of distally extending arms 211b, 211c and a bore 211d extending through the base and opening into a space between the arms. Each arm 211b, 211c includes an axle hole 211e, 211f for alignment with mounting holes 1503, 1505 of blades 1502 and 1504 for receiving a non-conductive screw 214 therethrough. The clevis base 211a is removably mounted within in the distal end 208b of the tube 208 and makes electrical contact therewith. The push rod 130 extends in a non-contacting manner through the bore 211d of the clevis 211 and distally terminates with an uninsulated flattened end 282 located between the clevis arms 211b, 211c. The blade members 1502, 1504 are mounted to the clevis 211 via screw 214 and coupled to the flattened distal end 282 of the push rod 130 with links 284, 286. In this way, cautery current applied to push rod 130 will be conducted through the links 284, 286 to the inner surfaces of blade members 1502, 1504.

The use of clevis 211 reduces the amount of space in the area of links 284, 286. Because of such reduced space, the blade members 1502, 1504 can be configured to couple with links 284, 286 about an inner surface 1502d, 1504d of an inner layer 1556, 1558 of the blades 1502, 1504, rather than about an outer surface of an inner layer of blades 102, 104 of the embodiment shown in FIGS. 10 through 12. Further, the interior surface of clevis 211 in the vicinity of the links 284, 286 may be insulated by anodizing or otherwise coating. Such a coating reduces short circuiting caused by contact of the links 284, 286 with the interior surfaces of the clevis 211.

Figure 16:
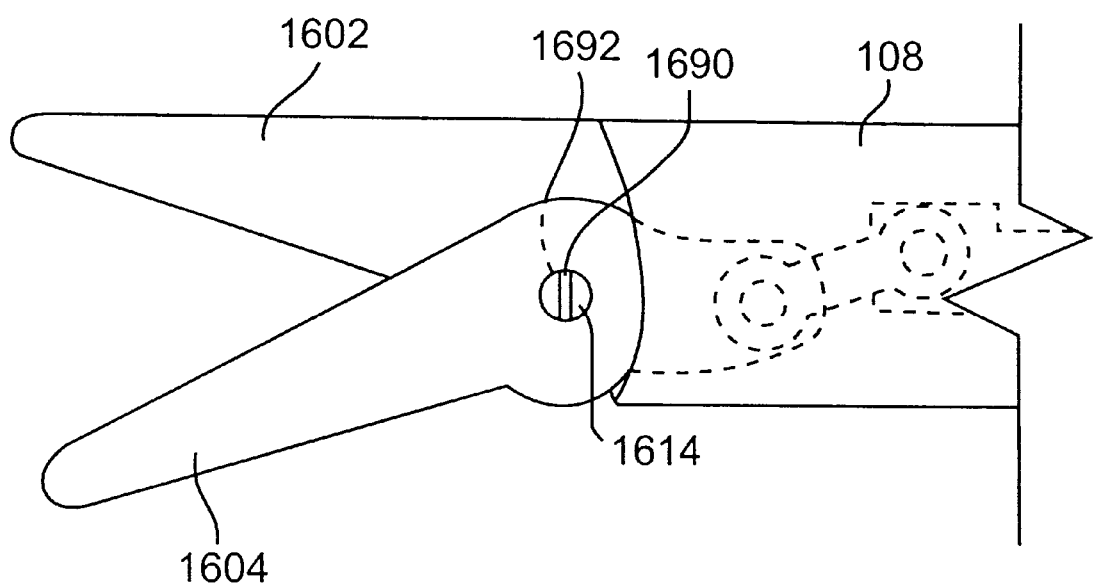
FIG. 16 is a partial section view of a third clevis arrangement for use in the embodiments of FIGS. 1 through 3.

FIG. 16 shows a third embodiment of a coupling arrangement of scissor blade members for use with the endoscopic electrocautery instruments of FIGS. 1 through 3. This arrangement incorporates a "single acting" blade configuration, wherein one blade member 1602 is fixed and the other blade member 1604 is actuated to rotate relative to the fixed blade member 1602. The fixed blade member 1602 is connected to the elongated tube 108 in any suitable manner, such as via a securing boss on fixed blade member 1602 in conjunction with a screw and boss receiving clevis, or integrally formed with the tube 108. Rotating blade member 1604 is rotatable about an insulated screw 1614 located in mounting holes 1690, 1692 of the rotating blade member 1604 and the fixed blade member 1602 or a clevis. The rotating blade member 1614 is coupled to a push rod in any of the manners previously described with reference to FIGS. 10–15 (as exemplified in phantom lines in the figure) and can be electrically connected to cautery current by way of the push rod and/or swiping contact with tube 108. Any of the blade configurations described with regard to FIGS. 4–9 may be used with this embodiment.

In operation, the coupling arrangement of FIG. 16 allows cautery current of a first polarity to travel from the push rod 130 to the rotating blade member 1604 and cautery current of an opposite polarity to flow from the tube 108 to the fixed blade member 1602. Such an arrangement reduces the required number of parts over those instruments having two moving blade members. Further, such a "single acting" coupling arrangement herein described may be utilized in endoscopic electrocautery instruments having end effectors other than scissor blade members, for example, instruments having end effectors formed as graspers, jaws, or the like.

It will be apparent to those skilled in the art that various modifications and variations can be made in the endoscopic electrocautery instruments of the present invention without departing from the scope or spirit of the invention. For example, the endoscopic electrocautery instruments have been described above in connection with endoscopic scissors. It is to be understood that endoscopic instruments having various types of end effectors, including graspers, jaws, or other like effectors, can be used in connection with the teachings of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscopic electrocautery instrument for performing surgery on tissue of a patient and passing current through the tissue to cause cauterization thereof, the instrument having a proximal end and a distal end and comprising:

a proximal actuator;

an elongated tube having a proximal end connected to the actuator and a distal end;

a push rod extending through the elongated tube and including a proximal end connected to the actuator;

first and second end effectors located adjacent the elongated tube distal end and connected to the push rod to provide relative movement of the first and second end effectors upon actuation of the proximal actuator;

a first current path passing cautery current from the instrument proximal end to an end effector first portion by a movable conductive rod having a proximal end coupled to a cautery current connector and a distal end slidably contacting a proximal end of the elongated tube; and a second current path insulated from the first current path and passing cautery current from the instrument proximal end to an end effector second portion, the second current path including the push rod.

2. The endoscopic electrocautery instrument of claim 1, wherein:

the first end effector includes the end effector first portion and the end effector second portion.

3. The endoscopic electrocautery instrument of claim 2, wherein:

the second end effector includes the end effector first portion and the end effector second portion.

4. The endoscopic electrocautery instrument of claim 1, wherein:

the first end effector is a first blade member and the second end effector is a second blade member and one of the first and second blade member includes:

an inner conductive layer having a cutting edge and an inner shearing surface forming the end effector second portion, an outer conductive layer forming the end effector first portion, and an intermediate non-conductive layer insulating the inner conductive layer from the outer conductive layer.

5. The endoscopic electrocautery instrument of claim 4, wherein:
the other of the first and second blade member includes:
an inner conductive layer having a cutting edge and an inner shearing surface forming the end effector second portion,
an outer conductive layer forming the end effector first portion, and
an intermediate non-conductive layer insulating the inner conductive layer from the outer conductive layer.

6. The endoscopic electrocautery instrument of claim 4, including:
an outer non-conductive layer covering substantially all exposed surfaces of the outer conductive layer of the at least one blade member.

7. The endoscopic electrocautery instrument of claim 6, wherein:
the outer conductive layer of the at least one blade member includes an exposed end strip for allowing cautery current to pass between the inner conductive layer and the outer conductive layer via the tissue to be cauterized.

8. The endoscopic electrocautery instrument of claim 4, wherein:
at least one of the inner conductive layer and the outer conductive layer is deposited metal.

9. The endoscopic electrocautery instrument of claim 4, wherein:
the intermediate non-conducting layer is anodized aluminum.

10. The endoscopic electrocautery instrument of claim 4, wherein:
the inner conducting layer and the outer conducting layer are interlocked by a protrusion extending from one of the inner conducting layer and the outer conducting layer into a complementary recess in the other of the inner conducting layer and the outer conducting layer.

11. The endoscopic electrocautery instrument of claim 4, wherein:
the other of the first and second blade member includes:
an inner conductive layer having a cutting edge and an inner shearing surface further forming the end effector second portion, and
an outer non-conductive layer.

12. The endoscopic electrocautery instrument of claim 4, wherein:
a proximal end of each of the first and second blade members includes a mounting hole and a proximal portion for coupling with the push rod; and
the elongated tube includes an integral clevis portion having distal holes for alignment with the mounting holes and insertion therethrough of a non-conductive screw.

13. The endoscopic electrocautery instrument of claim 4, wherein:
a proximal end of each of the first and second blade members includes a mounting hole and a proximal portion for coupling with the push rod; and
the elongated tube includes a separable clevis member having distal holes for alignment with the mounting holes and insertion therethrough of a non-conductive screw.

14. The endoscopic electrocautery instrument of claim 13, wherein:
an interior surface of the clevis member is insulated.

15. The endoscopic electrocautery instrument of claim 4, wherein:
the first blade member is fixed to the elongated tube and the second blade member is pivoted to affect a scissor action.

16. The endoscopic electrocautery instrument of claim 1, wherein:
a proximal end of each of the first and second end effectors includes a mounting hole and a proximal portion for coupling with the push rod;
the elongated tube includes an integral clevis portion having distal holes for alignment with the mounting holes and insertion therethrough of a non-conductive screw;
the first current path further includes the clevis portion and an outer surface of at least one of the first and second end effectors; and
the second current path further includes the end effector proximal portion and an inner surface of at least one of the first and second end effectors.

17. The endoscopic electrocautery instrument of claim 1, wherein:
a proximal end of each of the first and second end effectors includes a mounting hole and a proximal portion for coupling with the push rod;
the elongated tube includes a separable clevis member having distal holes for alignment with the mounting holes and insertion therethrough of a non-conductive screw;
the first current path further includes the clevis member and an outer surface of at least one of the first and second end effectors; and
the second current path further includes the end effector proximal portion and an inner surface of at least one of the first and second end effectors.

18. The endoscopic electrocautery instrument of claim 17, wherein:
an interior surface of the clevis member is insulated.

19. The endoscopic electrocautery instrument of claim 1, wherein:
the first end effector is fixed to the elongated tube and the second end effector is pivoted to rotate in relation to the first end effector; and
the end effector first portion includes an outer surface of at least one of the first and second end effectors.

20. The endoscopic electrocautery instrument of claim 1, wherein:
a push rod proximal end and the conductive rod proximal end are fixedly secured in a proximal collar by ultra violet curing material.

21. An endoscopic electrocautery instrument for performing surgery on tissue of a patient and passing current through the tissue to cause cauterization thereof, the instrument having a proximal end and a distal end and comprising:
a proximal actuator;
an elongated tube having a proximal end connected to the actuator and a distal end;
a push rod extending through the elongated tube and including a proximal end connected to the actuator;
first and second blade members located adjacent the elongated tube distal end and connected to the push rod to provide relative movement of the first and second blade members upon actuation of the proximal actuator, one of the first and second blade members including:
an inner conductive layer having a cutting edge and an inner shearing surface,
an outer conductive layer,
an intermediate non-conductive layer insulating the inner conductive layer from the outer conductive layer, and
an outer non-conductive layer.

22. The endoscopic electrocautery instrument of claim 21, wherein:
a first electric connection includes the elongated tube for supplying cautery current to an end effector first portion by a conductive rod having a proximal end coupled to a cautery connector and a distal end slidably contacting a proximal end of the elongated tube, and
a second electric connection includes the push rod for supplying cautery current to an end effector second portion.

23. The endoscopic electrocautery instrument of claim 21, wherein:
the outer non-conductive layer covers substantially all exposed surfaces of the outer conductive layer.

24. The endoscopic electrocautery instrument of claim 23, wherein:
the outer conductive layer is aluminum and the outer non-conductive layer is anodized aluminum of the outer conductive layer.

25. The endoscopic electrocautery instrument of claim 24, wherein:
the outer conductive layer includes an exposed end strip for allowing cautery current to pass between the inner conductive layer and the outer conductive layer.

26. The endoscopic electrocautery instrument of claim 21, wherein:
the inner conductive layer is metallic;
the intermediate non-conductive layer is one of an epoxy and ceramic;
the outer conductive layer is aluminum; and
an outer non-conductive layer is anodized aluminum of the outer conductive layer and covers all exposed surfaces of the outer conductive layer except for an end strip adjacent a cutting edge of the inner conductive layer and an area adjacent a blade member mounting hole.

27. The endoscopic electrocautery instrument of claim 21, wherein:
at least one of the inner conductive layer and the outer conductive layer is deposited metal.

28. The endoscopic electrocautery instrument of claim 27, wherein:
the deposited metal is aluminum.

29. The endoscopic electrocautery instrument of claim 21, wherein:
the intermediate non-conductive layer is ceramic; and
the inner conductive layer and the outer conductive layer are aluminum deposited on the intermediate non-conductive layer.

30. The endoscopic electrocautery instrument of claim 21, wherein:
the intermediate non-conducting layer is anodized aluminum.

31. The endoscopic electrocautery instrument of claim 21, wherein:
the inner conducting layer and the outer conducting layer are interlocked by a dovetail protruding from one of the inner conducting layer and the outer conducting layer into a complementary recess in the other of the inner conducting layer and the outer conducting layer.

32. The endoscopic electrocautery instrument of claim 21, wherein:
the inner conducting layer is aluminum;
the intermediate non-conducting layer is anodized aluminum of the inner conducting layer; and
the outer conducting layer is metallic and includes a dovetail for interlocking with a complementary recess in the inner conducing layer.

33. The endoscopic electrocautery instrument of claim 21, wherein:
the other of the first and second blade members includes:
an inner conductive layer having a cutting edge and an inner shearing surface, and
an outer non-conductive layer.

34. The endoscopic electrocautery instrument of claim 33, wherein:
the outer conductive layer is aluminum; and
the first blade member further includes an outer non-conductive layer of anodized aluminum of the outer conductive layer and covering substantially all exposed surfaces of the outer conductive layer.

35. The endoscopic electrocautery instrument of claim 33, wherein:
the outer conductive layer includes an exposed end strip for allowing cautery current to pass between the first blade member inner conductive layer and the outer conductive layer.

36. The endoscopic electrocautery instrument of claim 33, wherein:
the inner conductive layers are metallic;
the intermediate non-conductive layer is one of an epoxy and ceramic;
the second blade member outer non-conductive layer is ceramic;
the outer conductive layer is aluminum; and
the first blade member further includes an outer non-conductive layer of anodized aluminum of the outer conductive layer and covering all exposed surfaces of the outer conductive layer except for an end strip adjacent a cutting edge of the first blade member inner conductive layer and an area adjacent a blade member mounting hole.

37. The endoscopic electrocautery instrument of claim 21, wherein:
a first electric connection includes the elongated tube for supplying cautery current to an end effector first portion;
a second electric connection includes the push rod for supplying cautery current to an end effector second portion;
a proximal end of each of the first and second end effectors includes a mounting hole and a proximal portion for coupling with the push rod;
the elongated tube includes an integral clevis portion having distal holes for alignment with the mounting holes and insertion therethrough of a non-conductive screw;
the first electric connection further includes the clevis portion and an outer surface of at least one of the first and second end effectors; and the second electric connection further includes the end effector proximal portion and an inner surface of at least one of the first and second end effectors.

38. The endoscopic electrocautery instrument of claim 21, wherein:
   a first electric connection includes the elongated tube for supplying cautery current to an end effector first portion;
   a second electric connection includes the push rod for supplying cautery current to an end effector second portion;
   a proximal end of each of the first and second end effectors includes a mounting hole and a proximal portion for coupling with the push rod;
   the elongated tube includes a separable clevis member having distal holes for alignment with the mounting holes and insertion therethrough of a non-conductive screw;
   the first electric connection further includes the clevis member and an outer surface of at least one of the first and second end effectors; and
   the second electric connection further includes the end effector proximal portion and an inner surface of at least one of the first and second end effectors.

39. The endoscopic electrocautery instrument of claim 21, wherein:
   the first end effector is fixed to the elongated tube and the second end effector is pivoted to rotate in relation to the first end effector; and
   the end effector first portion includes an outer surface of at least one of the first and second end effectors.

* * * * *